US008597698B2

(12) United States Patent
Reddy et al.

(10) Patent No.: US 8,597,698 B2
(45) Date of Patent: *Dec. 3, 2013

(54) FORMULATIONS FOR TREATMENT OF SKIN DISORDERS

(75) Inventors: N. B. Baktha Reddy, Chennai (IN); Vilambi Nrk Reddy, Cranbury, NJ (US); Anil Torgalkar, Cranbury, NJ (US); Nachalur Rengagamy Murugan, Trichy (IN); Senthil Kumar, Trichy (IN)

(73) Assignee: APPTEC, Inc., Cranbury, NJ (US)

( * ) Notice: Subject to any disclaimer, the term of this patent is extended or adjusted under 35 U.S.C. 154(b) by 45 days.

This patent is subject to a terminal disclaimer.

(21) Appl. No.: 13/615,506

(22) Filed: Sep. 13, 2012

(65) Prior Publication Data

US 2013/0017279 A1 Jan. 17, 2013

Related U.S. Application Data

(63) Continuation of application No. 12/317,642, filed on Dec. 23, 2008, now abandoned, and a continuation of application No. 12/286,564, filed on Sep. 30, 2008, now abandoned, and a continuation of application No. 12/009,799, filed on Jan. 22, 2008, now abandoned.

(51) Int. Cl.
*A61K 31/00* (2006.01)

(52) U.S. Cl.
USPC ....................................................... 424/725

(58) Field of Classification Search
None
See application file for complete search history.

(56) References Cited

U.S. PATENT DOCUMENTS

| 4,235,889 | A | 11/1980 | Evers |
| 5,165,932 | A | 11/1992 | Horvath |
| 5,858,372 | A | 1/1999 | Jacob |
| 6,011,067 | A | 1/2000 | Hersh |
| 7,666,450 | B2 | 2/2010 | Reddy et al. |
| 2005/0084547 | A1 | 4/2005 | Subbiah |
| 2005/0452996 | | 7/2005 | Butler |

FOREIGN PATENT DOCUMENTS

| CA | 2245254 A1 * | 3/2000 |
| JP | 07138174 | 5/2005 |

OTHER PUBLICATIONS

Krishnamurty et al. Clinical Study of Vetapalai from Journal of Research in Ayurveda and Siddha. vol. 2, No. 1 (1982) 58-66.*
Abu Ali Ibn Sina obtained from TDKL website. "AH1/77 Baan" from Al-Qaaanoon-fil-Tibb, vol. II, p. 72.*
Mathieu, B. "Copra Farming". Internet Archive Date: Jul. 31, 2001 [Retrieved from the Internet on: May 15, 2013]. Retrieved from: <URL: http://web.archive.org/web/20010731065507/http://www.com.univ-mrs.fr/IRD/atollpol/resatoll/coprah/utilcopr/ukculcop.htm>.*
Marriott et al. "Paraffin Ointment BP" found in Chapter 5: Extemporaneous dispensing in "Pharmaceutical Compounding and Dispensing" 2006, p. 76.*
Abu Ali Ibn Sina. 1000 year old reference. "AH1/77 Baan" from Al-Qaaanoon-fil-Tibb, vol. II, p. 72. Retrieved from TKDL on: May 16, 2013.*
Armstrong, Eric, "Coconut Oil: Miracle Medicine and Diet Pill," Retrieved from the Web: http://web.archive.org/web/20040403191338/http://www.coconut-connections.com/skin_care.htm.
Cordoro, K., "Topical Therapy for the Management of Childhood Psoriasis: Part I," \http://www.skintherapyletter.com/2008/13.3/1.html.
Ghosh, et.al., "Anti-Inflammatory Analgesic and Antipyretic Activities of 777 Oil—A Siddha Medicine," Bulletin of Medico-Ethano-Botanical Research (B.M.E.B.R.), vol. VI, No. 2 to 4 (1985) pp. 141-154.
Hipp, "Philippine Copra and Coconut Oil: Copra Production Methods Remain Primitive, Although Modern Machinery Has Been Applied in Crushing Plants," Oil & Fat Industries (Apr. 1931) 131-134.
"Youthing Strategies: Why Sesame Seed Oil is Kinown as the Queen of Oils," Internet Archive Date: Jul. 7, 2004 http://web.archive.org/web/20040707082230/http://youthingstrategies.com/qualities.htm.
"Principles of Skin Therapy: Common Types of Topical Formulations," Internet Archive Date: Aug. 25, 2003 http://web.archive.org/web/20030825162802/http://www.dermweb.com/therapy/common.htm.
"Virgin Coconut Oil and Your Skin," Adapted from Bruce Fife's book, The Healing Miracles of Coconut Oil., Copyright 2001 http://web.archive.org/web/20040403191338/http://www.coconut-connections.com/skin_care.htm.
Hoare, C; Li Wan Po A.; Williams H., (2000), "Systematic Reviews of Treatments for Atopic Eczema," Health Technology Assessment 4, 1-191.
Federman, D.; Froelich, C., "Topical Psoraisis Therapy," American Family Physician, Feb. 15, 1999.
Schwartz, R.; Januez, C.; Janniger, C., "Seborrheic Dermatitis: An Overview," American Family Physician, Jul. 1, 2006.
Luba, K; Stulberg, D., "Chronic Plaque Psoriasis," American Family Physician 73(4): 636-44, Feb. 15, 2006.
Lebwohl, M; Ting, P.T.; Koo, Jy M., "Psoriasis Treatment: Traditional Therapy," Ann. Rheum. Dis. 64 (Suppl 2), 2005.
Griffiths, C.; Voorhees, J. "Psoriasis, T Cells and Autoimmunity," J. R. Soc. Med. 89(6): 315-9 (1996).

(Continued)

*Primary Examiner* — Amy L Clark
(74) *Attorney, Agent, or Firm* — Stanley H. Kremen (57) ABSTRACT

The Present Invention teaches herbal formulations based on a non-aqueous extract of wrightia tinctoria and an extract of cocos nucifera, which, when applied topically and used as directed in therapeutically effective amounts, have been clinically proven to be safe and effective for people needing treatment for skin conditions such as reducing or regressing dermal tortuosity, reducing spongiform pustules, and reversing and regressing stratum granulosum in keratinization disorders. The formulations can take the form of an ointment, an oil, a soap, or a shampoo.

11 Claims, 5 Drawing Sheets

(56) References Cited

OTHER PUBLICATIONS

Hunziker, T; Schmidt, J., "Psoriasis, An Autoimmune Disease?" THER UMACH, (Feb. 1993) 50(2):110-3, Abstract Only, Article in German.

* cited by examiner

FIG. 1

Dermal Vessel Tortuosity – Before and After Treatment with Composition of Invention

Before
(Tortuous Vessels with
mononuclear infiltrate)

After 12 weeks
(Normal Vessels / dermis
Absence of acanthosis)

FORMULATIONS FOR TREATMENT OF SKIN DISORDERS

CROSS REFERENCE TO RELATED APPLICATIONS

This Present Application is a continuation of U.S. patent application Ser. No. 12/009,799 filed on Jan. 22, 2008, entitled "Compositions for the Regression of Dermal Vessel Tortuosity," which in turn is a continuation-in-part (CIP) of U.S. patent application Ser. No. 11/288,923 filed on Nov. 28, 2005, entitled "Compositions for Safe and Effective Regression of Dermal Vessel Tortuosity." The Present Application claims the benefit of and priority to both applications Ser. Nos. 12/009,799 and 11/288,923, which are incorporated by reference herein in their entirety.

The Present Application is also a continuation of U.S. patent application Ser. No. 12/286,564 filed on Sep. 30, 2008, entitled "Compositions for the Regression of Spongiform Pustules," which in turn is a continuation-in-part (CIP) of U.S. patent application Ser. No. 11/395,944 filed on Mar. 31, 2006, entitled "Compositions for the Safe and Effective Regression of Spongiform Pustules." The Present Application claims the benefit of and priority to both applications Ser. Nos. 12/286,564 and 11/395,944, which are also incorporated by reference herein in their entirety.

The Present Application is further a continuation of U.S. patent application Ser. No. 12/317,642 filed on Dec. 23, 2008, entitled "Compositions for the Reversal of Stratum Granulosum in Keratinization Disorders," which in turn is a continuation-in-part of U.S. patent application Ser. No. 11/731,345 filed on Mar. 31, 2007, entitled "Compositions for Safe and Effective Reversal of Stratum Granulosum in Keratinization Disorders," which in turn is a continuation-in-part of U.S. patent application Ser. No. 11/288,923 (previously cited above), entitled "Compositions for Safe and Effective Regression of Dermal Vessel Tortuosity." The Present Application claims the benefit of and priority to both applications Ser. Nos. 12/317,642 and 11/731,345, which are further incorporated by reference herein in their entirety.

The Present Application combines and consolidates the disclosures of U.S. patent applications Ser. Nos. 12/009,799, 12/286,564, and 12/317,642. No new matter has been added.

FIELD OF THE INVENTION

The Present Application relates to herbal formulations that are applied topically for treatments of various skin conditions. These treatments comprise, inter alia, the regression of dermal vessel tortuosity, the regression of spongiform pustules, and the reversal of stratum granulosum in keritinization disorders in psoriatic lesions.

BACKGROUND

The skin is made up of two primary layers that differ in function, thickness, and strength. From outside to inside, they are the epidermis and its sub-layers, and the dermis, after which is found subcutaneous tissue, or the hypodermis.

The epidermis of the skin is a non-vascularized layer of the skin. Different factors can result in increased blood vessel formation in the papillary dermis and these blood vessels may sometimes extend into the epidermis resulting in clinically significant skin manifestations. For example, over-activated keratinocytes actively producing and secreting pro-angiogenic factors in the form of growth factors or cytokines can result in increased blood vessel formation in the papillary dermis, which may sometime extend into the epidermis. Epidermal microvascular proliferation ultimately leads to epidermal keratinocyte hyperproliferation, thickening of the epidermis with parakeratosis of the stratum corneum and inflammatory infiltrate around the blood vessels in the papillary dermis. The microvascular changes are also characterized by increased tortuosity of dermal capillary loops which precede the development of epidermal hyperplasia.

Histological studies, including immunocytochemistry, routine histology and electron microscopy have clearly established that alterations in the blood vessel formation of the skin discussed above are a prominent feature in chronic inflammatory skin conditions, including psoriasis, eczema, rheumatoid arthritis, burn granulations, and hypertrophic scars. In psoriasis, for example, there is a marked increase in the cutaneous blood active edge of the psoriatic plaque [Braverman I M, Yen A. Ultrastructure of the capillary loops in the dermal papillae of psoriasis. J Invest Dermatol 1977: 68: 53-60].

The regression of dermal vessel tortuosity and of spongiform pustules in patients suffering from chronic inflammatory skin conditions provides the patient with benefits including but not limited to: reduced inflammation, reduced inflammatory edema, reduced erythema, reduced pain, reduced itching, help in resolving lesions and assistance in changing the epidermis to its normal non-vascularized state.

The epidermis, the outermost layer of skin, is thin but complex. Melanin, which is responsible for skin pigmentation, is found throughout the epidermis. The epidermis also keratinizes to produce nails, hair, sweat, and to regenerate.

Keratinization, the maturation and migration of skin cells, begins in the innermost layer of the epidermis, the stratum germinativum. These cells, called keratinocytes, accumulate and move outward toward the next epidermis layer, the stratum spinosum, where they become dense. The next layer, known as the stratum granulosum layer, contains 1 to 3 rows of flattened cells whose cytoplasm contain small granules. The granules contain proteins being transformed into the waterproofing protein keratin. It is in this layer that one finds glycolipids and a thickening of the membrane. A protein called filigrin is made in this layer and is put in the granules. In this layer, cells lose their nuclei. In the cytoplasm, there are keratohyalin granules as well as membrane-coating granules which expel their lipid contents into the intercellular spaces. Lipids assist in the formation of water barriers among the cells of the skin, which, in turn, help to ensure body moisturization. At this point, the cell also becomes flattened, or horny, and the nucleus disappears; what remains is keratin. In the next layer, the stratum lucidum, the cell is prepared to move into its final sub-layer with the addition of melanin granules. Then, sudden changes in enzyme function cause cell death. The products of this ongoing process form the stratum corneum, which is the outermost epidural layer consisting of neatly packed dead horny cells.

Keratinization disorders in the stratum granulosum layer in the epidermis can often lead to clinically significant skin manifestations. One common disorder includes thinning of the stratum granulosum layer due to malfunctioning of the keratinization process leading to reduction in the moisture barrier properties of the stratum granulosum layer. In addition, for example, over activated keratinocytes actively producing and secreting pro-angiogenic factors in the form of growth factors or cytokines can result in increased blood vessel formation in the papillary dermis which may sometime extend into the epidermis. Epidermal microvascular proliferation ultimately leads to epidermal keratinocyte hyperproliferation, thickening of the epidermis with parakeratosis of the stratum corneum and inflammatory infiltrate around the blood vessels in the papillary dermis. The microvascular changes are also characterized by increased tortuosity of dermal capillary loops which precedes the development of epidermal hyperplasia. Mitotic activity in the basal and suprabasal cells are greatly increased [Dr. George Jacob, Seminar on Psoriasis, Dubai, January 2001]. Cellular invasion takes place, particularly in the suprapapillary region to form the Munro 'micro abscess' which are extruded in the horny layer or they may collect in disintegrated malphigian cells, the cytoplasm of which had been lysed to form the multilocular or stratum granulosum of Kogoj.

Stratum granulosums of Kogoj are multilocular pustules in the upper stratum malpighii within a sponge-like network made up of flattened keratinocytes [M. S. Stone and T. L. Ray, DermPath Tutor, Department of Dermatology, Iowa College of Medicine, September 19951. They are seen in psoriasis, Reiter's disease, geographic tongue and rarely in candidiasis. Histological studies, including immunocytochemistry, routine histology and electron microscopy have clearly established that alterations in the blood vessel formation of the skin discussed above are a prominent feature of psoriasis and there is a marked increase in cutaneous blood active edge of the psoriatic plaque [Braverman I M, Yen A. Ultrastructure of the capillary loops in the dermal papillae of psoriasis. J Invest Dermatol 1977: 68: 53-60].

Numerous therapies in the field of allopathy medicine have been researched and developed to reduce dermal vessel tortuosity, to reduce spongiform pustules, and to reduce stratum granulosum disorder, especially in relation to psoriasis.

Treatment of psoriasis-Part I-Topical Therapy and Phototherapy, Mark Lebwohl, MD, et all American Academy of Dermatology, October 2001 Vol 45 (4).

Treatment of psoriasis-Part 2-Systemic Therapies, Mark Lebwohl, MD, et al, American Academy of Dermatology, November 2001 Vol 45(5).

The immunological basis for the treatment of psoriasis with new biological agents. James. G. krueger, M.D, American Academy of Dermatology, June 2002 Vol 46(1) Pages 1-26.

New psoriasis treatments based upon a deeper understanding of the pathogenesis of psoriasis vulgaris and psoriatic arthritis. Jeffrey. P. Callen et al, American Academy of Dermatology, August 2003 Vol 49(5) Pages 351-356.

However, most of these therapies provide only temporary symptomatic relief and are either unsatisfactory or very expensive and are associated with either short term or long term undesired side effect profiles. [National Psoriasis Conference, Boston Plaza Hotel, Aug. 5-8, 2005, Boston, Mass., USA.]

It is well-known that herbal formulations often have fewer undesirable side effect profiles and hence provide a viable alternative therapy to manage the chronic inflammatory skin conditions that exhibit dermal vessel tortuosity. Research efforts to develop herbal formulations to treat these conditions have been on the rise and there is a continuing need to develop herbal formulations to treat dermal vessel tortuosity, spongiform pustules, and stratum granulosum in keratinization disorders with minimal or no side effects.

Chopra, R. N., Nayar, S. C., and Chopra I. C., Glossary of Indian Medicinal Plants, C.S. I. R., P. 259, 1956.

Murugesa Mudaliar, K. S., Gunapadam (Material Medica) Vegetable Section, Govt. of TamilNadu, P. 527 (1969).

Venkatarajan, S., Sarabendra Vaithiya Muraigal, P. 160, 161 & 167 (1965).

Wealth of India, Raw Materials, Vol. X, P. 588-590, CSIR., New Delhi (1976).

Yugimuni Vaidya Chintamani (800) Stanza 494-51 8, 6. Rathina Nayakar & Sons, Madras, India.

Nair, C. P. R., Kurup, P. B., Pillai, K. G. B., Geetha, A., and Ramiah, N., Effect of Nimbidin in Psoriasis, Indian Medical Journal, October 1978.

SUMMARY OF THE INVENTION

The Present Invention teaches herbal formulations, developed by a dermatologist, based on wrightia tinctoria and an extract of cocos nucifera, which, when topically applied and used as directed in therapeutically effective amounts, have been clinically proven to be safe and efficacious for humans needing treatment, inter alia, in reducing or regressing dermal tortuosity, in reducing spongiform pustules, and in reversing and regressing stratum granulosum in keratinization disorders.

The definition of the term herb, as it is used here is taken from the definition provided by the Herb Society of America: The tem herb refers to a wide range of plants, including perennials, trees, shrubs, annuals, vines, and more primitive plants, such as ferns, mosses, algae, lichens, and fungi. The herbs are valued for their flavor, fragrance, medicinal and healthful qualities, economic and industrial uses, pesticidal properties, and coloring materials (dyes)." [Bown, Deni. The Herb Society of America New Encyclopedia of Herbs and Their Uses. New York: Dorling Kindersley, 2001, p. 18]

The formulations can take the form of an ointment, an oil, a soap, or a shampoo. It is comprised of a non-aqueous herbal extract of wrightia tinctoria, an herbal extract of cocos nucifera, and suitable pharmaceutically or cosmetically acceptable excipients designated for topical use in humans.

DETAILED DESCRIPTION OF THE INVENTION

The Present Invention relates to herbal formulations, which unexpectedly provide statistically superior efficacy as compared to allopathy control formulations in the reduction of dermal vessel tortuosity, in the reduction of spongiform pustules (spongiform pustules of Kogoj), and in the reversal of stratum granulosum disorder. The spongiform pustules may be one of the symptoms presented in a case of psoriasis, especially generalized pustular psoriasis. These formulations are applied topically, and are safe when used as directed. The Present Invention teaches an herbal composition that comprises a non-aqueous extract of wrightia tinctoria, an herbal extract of cocos nucifera, and pharmaceutically or cosmetically acceptable excipients suitable for topical use. The composition can be formulated as an ointment, an oil, a soap and a shampoo, and, when a therapeutic amount is applied topically to the affected area, in a therapeutically effective amount, it is effective in the treatment of dermal vessel tortuosity and is safe in humans.

The Present Invention also teaches the use of a non-aqueous medium, which is a non-volatile oil, wherein the non-volatile oil is preferably a vegetable oil such as coconut oil, gingely oil (sesame oil), sunflower oil, corn oil, refined vegetable oil or a combination of oils. The non-volatile oil in the extract of the present invention comprises from about 80% to 99% by weight of the extract.

The herbal extract in the topical formulation is derived from the wrightia tinctoria plant, especially the leaves, twigs, flowers, fruits or a combination of these parts of the plant. Wrightia tinctoria is an apocynaceae tree growing throughout India. Its flowers are white and fragrant.

The Present Invention further teaches a process for preparing the non-aqueous extract of wrightia tinctoria. The non-aqueous extract is prepared at ambient temperature by cleaning and pulverizing the selected parts of the wrightia tinctoria plant and soaking them in a non-aqueous oil medium containing coconut oil. Care should be taken to add sufficient oil medium to ensure that the plant material is completely submerged. The plant material/oil medium is then irradiated with a light source in the spectrum range of 300-1,100 nanometers for a period of approximately 5 days. During this time, the herbal ingredients are allowed to extract into the non-aqueous oil medium. At the end of the extraction, the oil medium is a purplish brown color. It is then filtered and the filtrate is stored for further processing as the non-aqueous herbal extract of wrightia tinctoria.

Other herbal extracts may optionally be included in the formulation, among them being melia azadirachta Linn oil (Neem oil), which has been documented to have beneficial skin effects [Nair et al., 1978]. The topical composition of the Present Invention comprises an extract of the active herbal ingredient mentioned above in the extraction medium in the amount from 1% to 20% by weight.

The herbal extract of cocos nucifera in the formulations of the Present Invention is derived from the copra of the coconut. The copra of the coconut is dried and then processed by grinding and pressing to extract the oil, which is then purified and stabilized. The herbal composition of the present invention comprises the herbal extract (the oil) of cocos nucifera present in the amount of 40% to 80% by weight.

In addition, the Present Invention teaches formulations for topical use by further compounding the compositions with ingredients mentioned herein to prepare formulations, including but not limited to, an ointment, an oil, a liquid soap and a shampoo.

The ointment formulation of the herbal composition of the Present Invention is suitable, when used topically in a therapeutically effective amount. It includes pharmaceutically acceptable excipients such as beeswax, paraffin (liquid, soft and hard), and other standard ointment bases or their equivalents to optimize the use characteristics of the formulations, such as consistency and spreadabilrty, as well as manufacturability and stability. The ointment composition comprises one or more of the excipients including beeswax, optimally present in the amount of 1 to 5% by weight; paraffin, optimally present in the amount of 5 to 40% by weight; and standard ointment bases, optimally present in the amount of 5 to 50%. by weight.

The oil formulation of the herbal composition of the Present Invention is suitable, when used topically in a therapeutically effective amount. It includes pharmaceutically acceptable excipients such as vegetable oil, animal oil, and synthetic oils such as mineral oil and liquid paraffin or their equivalents to optimize the use characteristics of the formulations, such as consistency and spreadability, as well as manufacturability and stability. Preferably, the oil composition comprises excipients, such as coconut oil, present in the amount of 70 to 95% by weight.

The liquid soap formulation of the herbal composition of the invention Is suitable, when used topically in a therapeutically effective amount. It includes pharmaceutically acceptable excipients, including but not limited to: water, surface active agents, thickeners and viscosity enhancers, foam boosters, and stabilizers to optimize the use characteristics, such as consistency, cleaning, spreadability and foaming, as well as manufacturability and stability. The liquid soap formulation of the Present Invention perferably comprises excipients such as water present in the amount of 60 to 85% by weight; surface active agents present in the amount of 5 to 40% by weight; thickeners or viscosity enhancers present in the amount of 0.5 to 8% by weight; foam boosters present in the amount of 1 to 4% by weight; and stabilizers present in the amount of 0.5 to 2% by weight.

The shampoo formulation of the herbal composition of the Present Invention Is suitable, when used topically in a therapeutically effective amount. It includes pharmaceutically acceptable excipients, comprising water, surface active agents, thickeners or viscosity enhancers, foam boosters, and stabilizers to optimize the use characteristics such as consistency, cleaning, spreadability and foaming, as well as manufacturability and stability. The shampoo composition of the Present Invention preferably comprises excipients including water present in the amount of 50 to 85% by weight; surface active agents present in the amount of 10 to 30% by weight; thickeners or viscosity enhancers present in the amount of 2 to 8% by weight; foam boosters present in the amount of 2 to 6% by weight; and stabilizers present in the amount of 0.5 to 2% by weight.

In addition, the ointment, oil, liquid soap and shampoo formulations of the herbal composition of the invention are suitable, when used topically in a therapeutically effective amount. They optionally comprise preservatives, coloring agents and fragrances as needed, wherein the preservatives, coloring agents and fragrances are present in the amount of 0 to 5 total weight percent.

Safety and efficacy studies were conducted on subjects exhibiting dermal vessel tortuosity using topical formulations of the herbal composition of the present invention described above, containing a non-aqueous herbal extract of wrightia tinctoria, an herbal extract of cocos nucifera and pharmaceutically or cosmetically acceptable excipients. Patients suffering from chronic inflammatory skin conditions selected for the study exhibited dermal vessel tortuosity in the form of psoriatic lesions. Psoriasis is a representative example of dermal vessel tortuosity. Patients selected for the study also included those exhibiting spongiform pustules in the form of psoriatic lesions. Psoriasis is a representative example of spongiform pustules. They also included those exhibiting straum granulosum in keritinization disorders in the form of psoriatic lesions. Psoriasis is a representative example of a condition exhibiting stratum granulosum in keritinization disorders. The results are illustrated by the following example.

EXAMPLE

Twenty patients were enrolled in a clinical study and were divided into two groups of 10 patients each. Group I was treated with the herbal formulation (see Table 1 for details) once daily, and Group II was treated with an allopathy control formulation (see Table 2 for details) once daily. All patients were psoriasis patients.

TABLE 1

Herbal Ointment Formula

| No. | Ingredient | Quantity |
|-----|------------|----------|
| 1 | Wrightia Tinctoria | 5% |
| 2 | Cocos Nucifera | 65% |
| 3 | Bees Wax | 6% |
| 4 | Liquid Paraffin | 24% |

TABLE 2

Dithranol Ointment (Allopathy Control)

| No. | Ingredient | Quantity |
|-----|------------|----------|
| 1 | Dithranol | 1% |
| 2 | Standard Ointment Base | QS |

Assignment of patients to treatment groups was randomized as per standard statistical methods to minimize bias in the study. Patients were enrolled in the study on a first come, first served basis and assigned a subject number sequentially. The assignment of each patient to the treatment group was determined by the randomization list provided by the statistician.

Efficacy Evaluation

Each patient voluntarily enrolled in the study and received the treatment for 8 weeks. Skin biopsies at the treatment site were taken from all patients at the beginning (T0) and end of the study (T8w) for histopathological evaluation. In addition, at the beginning (T0), end of treatment (T8w) haemogram analysis, liver function testing and renal function testing were done to document the safety profile of the treatments administered.

Histopathology of the skin biopsy was done by an expert pathologist and the dermal vessel tortuosity parameter was measured at visits $T_0$ and $T_{8w}$. The results of the measurements were scored as follows:

(+)=3 representing significant tortuosity of the dermal vessels (±)=2 representing moderate tortuosity of the dermal vessels (−)=1 representing no tortuosity of the dermal vessels.

The dermal vessel tortuosity parameter represents the degree of tortuosity of the dermal vessels. The more active the disease, the more the tortuosity of the dermal vessels.

The spongiform pustule parameter represents the severity of infiltration in the epidermal cells. The more active the disease, the more severe the degree of infiltration The stratum granulosum parameter represents the thickness and integrity of the stratum granulosum layer. The more active the disease, the thinner the stratum granulosum layer and the lower the lipid content.

Figure 1:
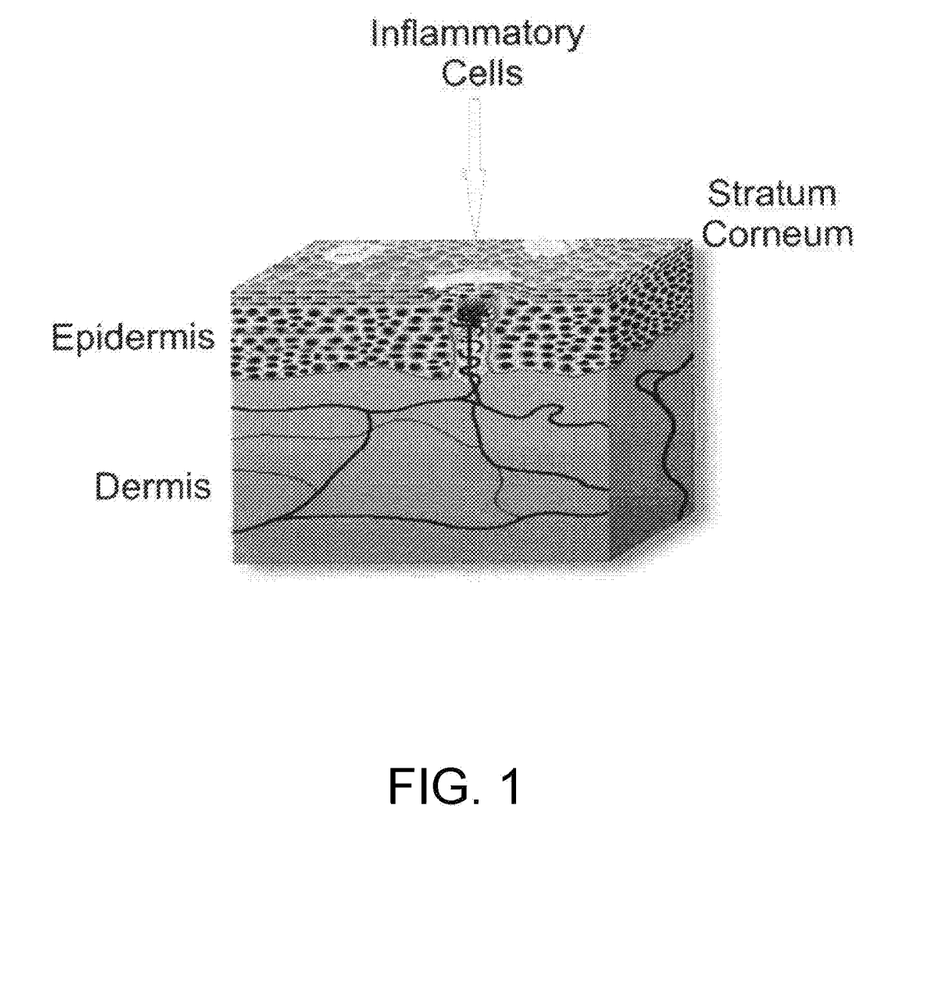
FIG. 1 is an illustration of epidermal microvascular proliferation.
Figure 2:
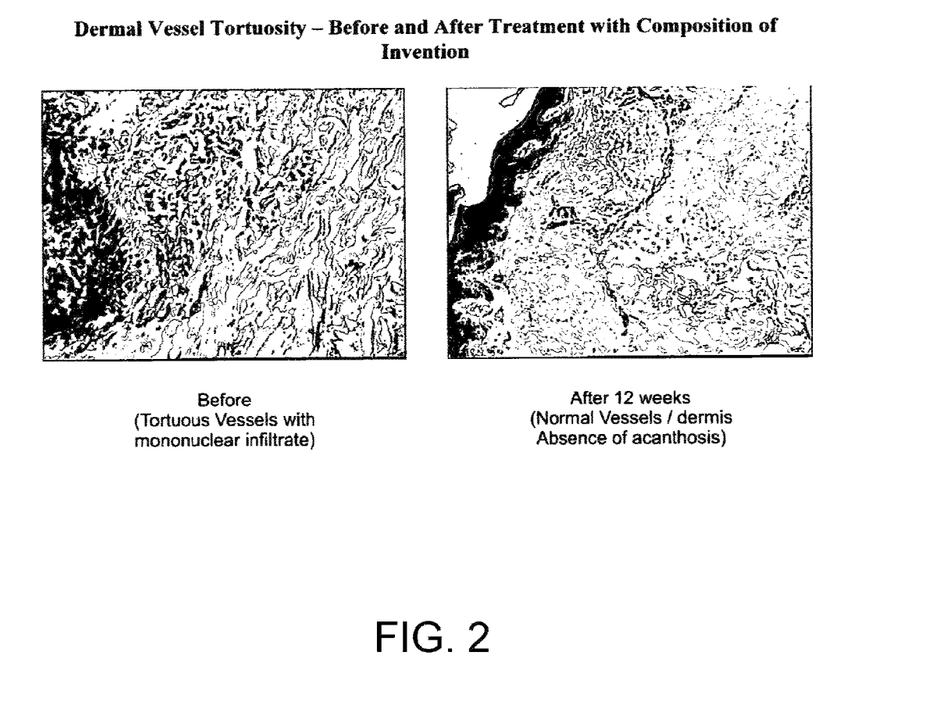
FIG. 2 shows micrographs of dermal vessel tortuosity before and after treatment with the herbal formulation.

FIG. 2 presents photomicrographs of patients observed before and after the 8-week treatment with the herbal formulation of wrightia tinctoria and cocos nucifera. It is clear from the photographs that the treatment with the herbal formulation is very effective in regressing the dermal vessel tortuosities and in clearing the dermal infiltrate as compared to the condition prior to the start of treatment.

Figure 3:
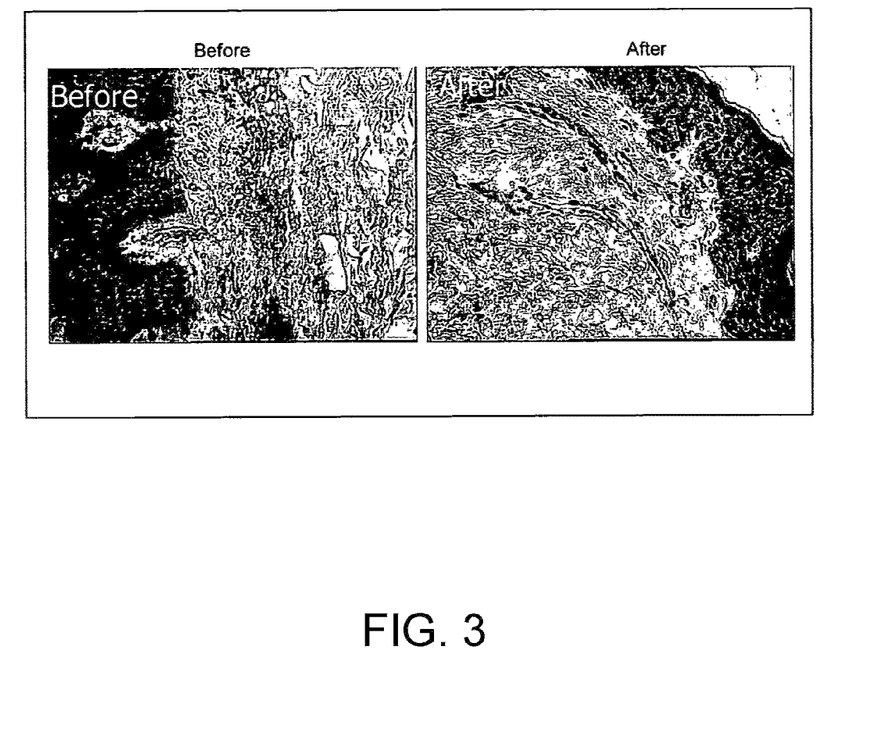
FIG. 3 shows micrographs of spongiform pustules before and after treatment with the herbal formulation.
Figure 4:
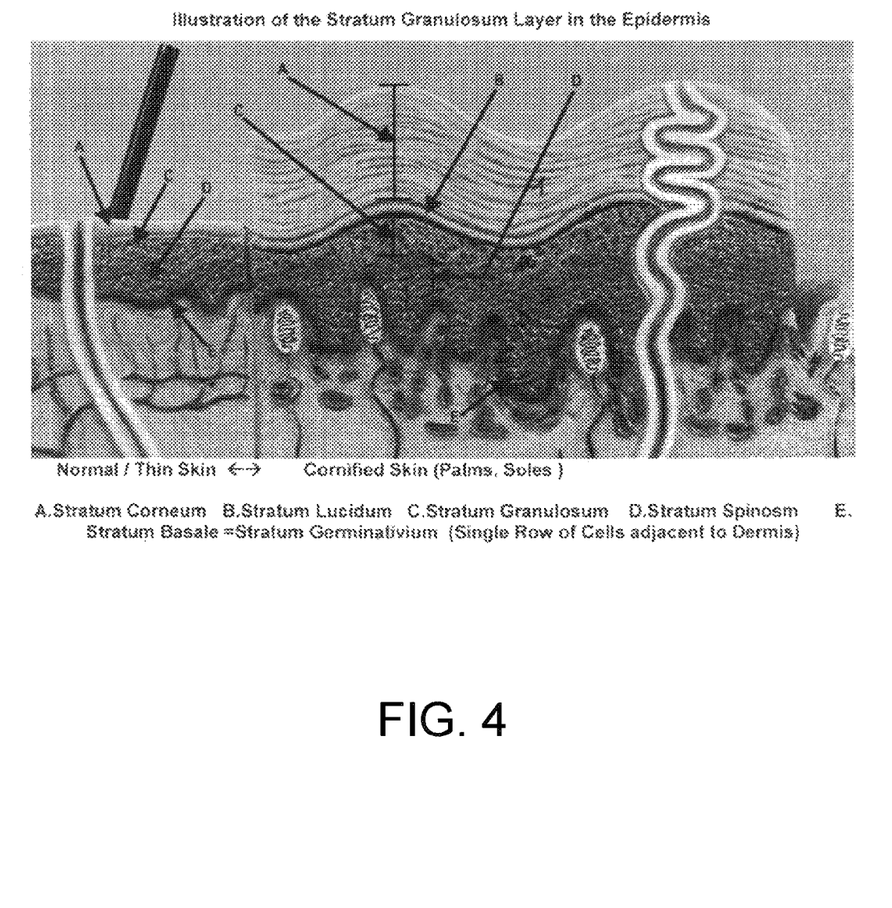
FIG. 4 is an illustration of the stratum granulosum layer in the epidermis.

FIG. 3 presents photomicrographs of patients observed before and after the 8-week treatment with the same herbal formulation. It is clear from the photographs that the treatment with the herbal formulation is very effective in regressing the spongiform pustules and in clearing the dermal infiltrate as compared to the condition of the patient prior to the start of treatment.

Figure 5:
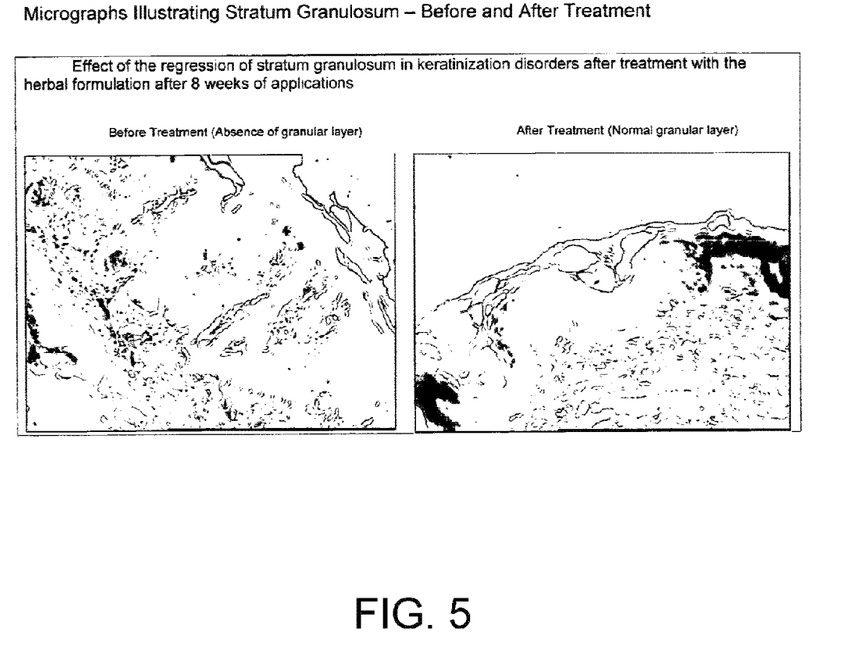
FIG. 5 shows micrographs illustrating stratum granulosum in keritinization disorders before and after treatment with the herbal formulation.

FIG. 5 presents photomicrographs of the skin of patients observed before and after the 8-week treatment with the same herbal formulation. It is clear from the photographs that the treatment with the herbal formulation is very effective in increasing the integrity and thickness of the stratum granulosum layer as compared to the condition prior to the start of treatment.

Results of the statistical analysis of the dermal vessel tortuosity measurement data for the 2 treatment groups are. presented in Table 3. A p-value of 0.05 is considered to be significant.

TABLE 3

Statistical Analysis of Histopathology Measurements for Dermal Vessel Tortuosity

|  | Herbal (Group I) | | Allopathy Control (Group II) | | | |
|---|---|---|---|---|---|---|
|  | Mean | SD | Mean | SD | t | P-Value |
| $T^{0w}$ | 3 | 0.67 | 2.70 | 0.67 | 1.406 | 0.177 |
| $T_{1w}$ | 1.70 |  | 1.90 | 0.99 | 0.526 | 0.605 |
| Paired t Statistic | 6.091 |  | 1.922 |  |  |  |
| Sig (2-tailed) | 0.001 |  | 0.867 |  |  |  |

To examine the treatment effects, a t-test was performed with the data taken for the two groups at the beginning and the end of the treatment. No statistical significance was observed (p>0.05) for treatment effects on the dermal vessel tortuosity measurements at the beginning (p=0.177) and the end of the treatment (p=0.605).

To examine the time effects within each group, a paired t-test was done with data at the beginning and the end of treatment within each group. With the herbal group, there was a statistically significant time effect (p-values equal to 0.001) on the dermal vessel tortuosity measurements and it was found that the dermal vessel tortuosity values decreased with time, suggesting a positive response to the herbal treatment with time. However, with the allopathy control (Group II), no statistically significant time effect was found for the allopathy control formulation (p-value equal to 0.087).

The statistical data analysis clearly indicates that the herbal treatment for the regression of dermal vessel tortuosity is effective and is superior to the allopathy control formulation.

Results of the statistical analysis of the spongiform pustule measurement data for the 2 treatment groups are presented in Table 4. A p-value of 0.05 is considered to be significant.

TABLE 4

Statistical Analysis of Histopathology Measurements Spongiform Pustule

|  | Herbal (Group I) | | Allopathy Control (Group II) | | | |
|---|---|---|---|---|---|---|
|  | Mean | SD | Mean | SD | t | P-Value |
| $T_{0w}$ | 2.00. | 1.05 | 1.60 | 0.97 | 0.885 | 0.388 |
| $T_{1w}$ | 1.00 | 0.00 | 1.00 | 0.00 | — | — |
| Paired t Statistic | 3.00 | 1.05 | 1.964 |  |  |  |
| Sig (2-tailed) | 0.001 |  | 0.087 |  |  |  |

To examine the treatment effects, a t-test was performed with the data taken for the two groups at the beginning and the end of the treatment. No statistical significance was observed (p>0.05) for treatment effects on the spongiform pustule measurements at the beginning (p=0.388) and the end of the treatment (no difference in values between treatments).

To examine the time effects within each group, a paired t-test was done with data at the beginning and the end of treatment within each group. With the herbal group, there was a statistically significant time effect (p-values equal to 0.015) on the spongiform pustule measurements and it was found that the spongiform pustule values decreased with time, suggesting a positive response to the herbal treatment with time. However, with the allopathy control (Group II), no statistically significant time effect was found for the allopathy control formulation (p-value equal to 0.081).

The statistical data analysis dearly indicates that the herbal treatment for the regression of spongiform pustule is effective and is superior to the allopathy control formulation.

Results of the statistical analysis of the stratum granulosum measurement data for the two treatment groups are presented in Table 5. A p-value of 0.05 is considered to be significant.

TABLE 5

Statistical Analysis of Histopathology Measurements for Stratum Granulosum

|  | Herbal (Group I) | | Allopathy Control (Group II) | | | |
| --- | --- | --- | --- | --- | --- | --- |
|  | Mean | SD | Mean | SD | t | P-Value |
| $T_{0w}$ | 2.00. | 0.94 | 1.6 | 0.84 | 1.000 | 0.331 |
| $T_{1w}$ | 1.00 | 0.00 | 1.2 | 0.63 | 1.000 | 0.331 |
| Paired t Statistic | 3.354 | | 1.078 | | | |
| Sig (2-tailed) | 0.008 | | 0.309 | | | |

To examine the treatment effects, if any, a t-test was performed with the data taken for the two groups at the beginning and the end of the treatment. No statistical significance was observed (p>0.05) for treatment effects on the stratum granulosum measurements at the beginning (p=0.388), and the end of treatment. That is, no difference in values could be attributed to the different treatments).

To examine the time effects within each group, a paired t-test was done with data at the beginning and end of treatment within each group. With the herbal group, there was a statistically significant time effect (p-values equal to 0.015) on the stratum granulosum measurements, and it was found that the stratum granulosum values decreased with time suggesting a positive response to herbal treatment with time.

However, with the allopathy control (Group II), no statistically significant time effect was found for the Allopathy control formulation (p-value equal to 0.081).

The statistical data analysis clearly indicates that the herbal treatment for regression of stratum granulosum in keritinization disorders is effective and is superior to the allopathy control formulation.

Safety Evaluation

The safety of the use of the herbal formulation over the treatment period was evaluated by taking measurements of vital signs, haemogram measurements, liver function test (LFT) measurements, and renal function test (RFT) measurements and analyzing the data as a function of time.

The vital signs were measured 6 times during the treatment: T0, $T_{1w}$, $T_{2w}$, $T_{4w}$, $T_{6w}$, and $T_{8w}$; the haemogram, the LFT and RFT measurements were made only at the beginning and end of the treatment (T0, $T_{8w}$).

The results of the statistical analysis of the vital sign measurements (Systolic and Diastolic BPI pulse rate and respiratory measurements) are presented in Table 6. The BP was measured using a manual mercury sphygmomanometer. The unit of measurement is mm of Hg. The pulse rate was measured (beats per minute) in the radial artery by palpating the artery with the middle, .index and ring finger. The respiratory rate was measured by watching the expansion of the abdomen with each respiration and counting the expansions for one minute.

TABLE 6

Statistical Analysis of Vital Sign Measurements for Herbal Treatment

| Time Points | BP-Systolic | | BP-Diastolic | | Pulse Rate | | Respiratory Rate | |
| --- | --- | --- | --- | --- | --- | --- | --- | --- |
|  | Mean | SD | Mean | SD | Mean | SD | Mean | SD |
| 0w | 121.10 | 15.31 | 81.00 | 8.76 | 87.60 | 17.33 | 23.00 | 6.20 |
| $T_{1w}$ | 111.40 | 11.43 | 77.00 | 8.01 | 75.80 | 8.77 | 21.40 | 7.00 |
| $T_{2w}$ | 114.00 | 14.30 | 79.20 | 9.85 | 74.60 | 11.70 | 22.30 | 6.93 |
| $T_{4w}$ | 107.00 | 8.23 | 79.00 | 5.68 | 85.40 | 11.47 | 24.20 | 5.45 |
| $T_{6w}$ | 111.40 | 8.00 | 78.80 | 5.27 | 78.70 | 22.60 | 24.00 | 3.62 |
| $T_{8w}$ | 109.00 | 12.87 | 78.00 | 6.32 | 82.40 | 11.96 | 25.40 | 4.09 |
| Grand Mean | 112.32 | 12.36 | 78.83 | 7.28 | 80.75 | 14.88 | 23.38 | 5.72 |
| 1-Way ANOVA | 1.674 | | 0.317 | | 1.273 | | 0.612 | |
| F-value p-value | 0.157 | | 0.901 | | 0.289 | | 0.691 | |

A regular one-way ANOVA was also used to analyze the data at different time points for the vital signs measurements. The data clearly indicates that there were no statistically significant time effects on BP systolic measurements (p=0.157); BP diastolic measurements (p=0.901); pulse rate measurements (p=0.289) and respiratory rate measurements (0.691) with the herbal treatment. In summary, there is no statistically significant change in the vital sign measurements over time due to treatment with the formulation of the Present Invention, thereby suggesting no safety issues.

Results of the statistical analysis of the haemogram measurements [Total count of white blood cells (TC), differential white blood cells count as polymorphonuclear neutrophil (DC-P), lymphocytes (DC-L), eosinophils (DC-E) and hemoglobin (Hb)] are presented in Table 7. TC (Total count of white blood cells in the blood) was measured using a Neubauer Counting Chamber. The normal range for TC measurements is 4,000-11,000 cells per cubic millimeter. DC-P, which stands for the percentage of P-polymorphonuclear neutrophil, was measured using Neubauer Counting Chamber. The normal range for DC-P measurements is 55-65% of total white cell count. DC-L, which is the percentage of lymphocytes present, was measured using a Neubauer Counting Chamber. The normal range for DC-L Measurements is 30-40% of the total white cell count. DC-L was measured. DC-El which is the percentage of eosinophils, was measured using the Neubauer Counting Chamber. The normal range for DC-E measurements is 1-7% of the total white blood cell count. DC-E was measured. HB, which is the hemoglobin measurements, was measured using the RA 50 Biochemical Analyzer and the normal range is 12-14 gm.

TABLE 7

Statistical Analysis of Haemogram Measurements for Herbal Treatment

| Time Points | TC Mean | TC SD | DC-P Mean | DC-P SD | DC-L Mean | DC-L SD | DC-E Mean | DC-E SD | HB Mean | HB SD |
|---|---|---|---|---|---|---|---|---|---|---|
| T0w | 7343 | 1589 | 57.30 | 2.95 | 37.90 | 1.79 | 4.80 | 2.90 | 13.02 | 1.72 |
| T8w | 8634 | 1105 | 58.90 | 2.69 | 37.10 | 2.38 | 4.00 | 2.49. | 12.95 | 0.94 |
| Paired in differ mean | −1291 | 2279 | −1.60 | 3.78 | 0.80 | 3.22 | 0.80 | 3.77 | 0.075 | 2.13 |
| Paired t statistic | −1.791 | | −1.340 | | 0.784 | | 0.672 | | 0.100 | |
| Sig (2-tailed) | 0.107 | | 0.213 | | 0.453 | | 0.519 | | 0.924 | |

To examine the time effects, a paired t-test was done with data taken at the beginning and end of treatment for each of the haemogram measurements. The data clearly indicates that there were no statistically significant time effects on TC measurements (p=0.1 07); DC-P measurements (p=0.213); DC-L measurements (p=0.453); DC-E measurements (p=0.519) and HB measurements (p=0.924) with the herbal treatment. In summary, there is no statistically significant change in haemogram measurements with time due to the treatment with the herbal formulation, suggesting no safety issues.

Results of the statistical analysis of the liver function test (LFT) measurements [serum glutamic oxalo acetic transaminase (SGOT), serum glutamic pyruvic transaminase (SGPT) and serum bilirubin] are presented in Table 8. SGOT, serum glutamic—oxalo acetic transaminase (international unit per liter), was measured at visits To and Taw. The normal range is 0-46 IU/L. SGPT, serum glutamic pyruvic transaminase (international units liter) was measured at visits $T_0$ and $T_{8W}$. The normal SGPT ranges from 0 to 49 IU/L. The serum bilirubin was measured at visits $T_0$ and $T_{8W}$. The normal serum bilirubin ranges from 0.0 to 1.0 mg/dl.

TABLE 8

Statistical Analysis of Liver Function Test (LFT) Measurements for Herbal Treatment

| Time Points | SGOT Mean | SGOT SD | SGPT Mean | SGPT SD | Serum Bilirubin Mean | Serum Bilirubin SD |
|---|---|---|---|---|---|---|
| T0w | 24.90 | 8.80 | 26.10 | 14.78 | 0.73 | 0.23 |
| T1w | 24.00 | 8.94 | 26.60 | 11.01 | 0.89 | 0.24 |
| Paired in differ mean | 0.90 | 10.97 | −0.50 | 11.24 | 0.035 | 0.31 |
| Paired t Statistic | 0.259 | | 0.141 | | 0.352 | |
| Sig (2-tailed) | 0.801 | | 0.891 | | 0.733 | |

To examine the time effects a paired t-test was done with data taken at the beginning and the end of treatment for each of the LFT measurements. The data clearly indicates that there were no statistically significant time effects on SGOT measurements (p=0.801); SGPT measurements (p=0.891); and the serum bilirubin measurements (p=0.733) with the herbal treatment. In summary, there is no statistically significant change in LFT measurements with time due to treatment with the herbal formulation of the present invention for the regression of stratum granulosum in keritinization disorders, suggesting no safety issues.

Results of the statistical analysis of the Renal Function Test (RFT) measurements [serum creatinine and serum urea,] are presented in Table 9. Serum creatinine was measured at visits $T_0$ and $T_{8w}$. The normal serum creatinine value ranges from 0.8 to 1.4 mg/dl. Serum urea was measured at visits $T_0$ and $T_{8w}$. The normal serum urea value ranges from 10 to 50 mg/dl.

TABLE 9

Statistical Analysis of Renal Function Test (RFT) Measurements for the Herbal Treatment

| Time Points | Serum Creatinine Mean | Serum Creatinine SD | Serum Urea Mean | Serum Urea SD |
|---|---|---|---|---|
| T0 w | 1.06 | 0.22 | 32.40 | 17.50 |
| T8 w | 1.08 | 0.18 | 25.49 | 7.75 |
| Paired in differ mean | −0.021 | 0.244 | 6.91 | 18.81 |
| Paired t statistic | −0.271 | | −1.161 | |
| Sig (2-tailed) | 0.792 | | 0.275 | |

To examine the time effects paired t-test was done with data at the beginning and end of treatment for each of the RFT measurements. The data clearly indicates that there were no statistically significant time effects on serum creatinine measurements (p=0.792) and serum urea measurements (p=0.275) with the herbal treatment. In summary, there is no statistically significant change in RFT measurements with time due to treatment with the herbal formulation of the Present Invention for the regression of stratum granulosum in keritinization disorders, suggesting no safety issues.

It is clear from the histopathological examination and statistical analysis of the clinical data that the herbal formulations of the compositions of the Present Invention are very effective in the treatment of dermal vessel tortuosity, spongiform pustules, and stratum granulosum, and is superior to the allopathy control. In addition, the evaluation of haemogram, LFT and RFT test results clearly show that the herbal formula of the Present Invention is also safe to use on humans when used as directed.

Other modifications and variations of the present invention will become apparent to those skilled in the art from an examination of the above specification and examples. Therefore, other variations of the present invention may be made, which fall within the scope of the appended claims even though such variations were not specifically discussed above.

We claim:

1. A topical composition in the form of an ointment, an oil-based formulation, a liquid soap, or a shampoo for treating psoriasis in a person in need thereof comprising an effective amount of a formulation comprising:
   a) a *Wrightia tinctoria* extract in an amount ranging from 1% to 20% by weight, wherein said *Wrightia tinctoria* extract is obtained by extraction of leaves, twigs, flowers, and/or fruit of *wrightia tinctoria* with a non-volatile oil;
b) *Cocos nucifera* chopra oil in an amount ranging from 40% to 80% by weight, and,
c) *Melia azadirachta* oil in an amount ranging from 1% to 20% by weight, and
wherein, said topical formulation provides: regression of dermal vessel tortuosity; regression of spongiform pustules; and/or reversal of stratum granulosum in keritinization dorders when applied to human skin.

2. The topical composition of claim 1, wherein the *wrightia tinctoria* extract comprises between 80% to 99% of the non-volatile oil.

3. The topical composition of claim 1, wherein the non-volatile oil is a vegetable oil.

4. The topical composition of claim 3, wherein the vegetable oil is selected from the group consisting of coconut oil, sesame oil, sunflower oil, and corn oil.

5. The topical composition of claim 3, wherein the non-volatile vegetable oil is a combination of at least two oils are selected from the group consisting of coconut oil, sesame oil, sunflower oil, and corn oil.

6. The topical composition of claim 1, wherein the composition is in the form of an ointment and wherein the ointment further comprises:
 i) beeswax in an amount ranging from 1% to 5% by weight;
 ii) paraffin in an amount ranging from 5% to 40% by weight; and
 iii) standard ointment bases in an amount ranging from 5% to 50% by weight.

7. The topical composition of claim 1, wherein the composition is in the form of an oil-based formulation.

8. The topical composition of claim 1, wherein the composition is in the form of a liquid soap, wherein the liquid soap further comprises:
 i) water in an amount ranging from 60% to 85% by weight;
 ii) surface active agents in an amount ranging from 5% to 40% by weight;
 iii) thickeners or viscosity enhancers in an amount ranging from 0.5% to 8% by weight;
 iv) foam boosters in an amount ranging from 1% to 4% by weight; and
 v) stabilizers in an amount ranging from 0.5% to 2% by weight.

9. The topical composition of claim 1, wherein the composition is in the form of a shampoo, wherein the shampoo further comprises:
 i) water in an amount ranging from 50% to 85% by weight;
 ii) surface active agents in an amount ranging from 10% to 30% by weight;
 iii) thickeners or viscosity enhancers in an amount ranging from 2% to 8% by weight; and
 iv) stabilizers in an amount ranging from 0.5% to 6% by weight.

10. The topical composition of claim 1, wherein the composition further comprises preservatives, coloring agents, and fragrances present in an amount ranging from 0% to 5% by weight.

11. A topical composition in the form of an ointment, an oil-based formulation, a liquid soap, or a shampoo for treating psoriasis in a person in need thereof comprising an effective amount of a formulation consisting essentially of:
a) a *Wrightia tinctoria* extract in an amount ranging from 1% to 20% by weight, wherein said *Wrightia tinctoria* extract is obtained by extraction of leaves, twigs, flowers, and/or fruit of *wrightia tinctoria* with a non-volatile oil;
b) *Cocos nucifera* chopra oil in an amount ranging from 40% to 80% by weight, and,
c) *Melia azadirachta* oil in an amount ranging from 1% to 20% by weight, and
wherein, said topical formulation provides: regression of dermal vessel tortuosity; regression of spongiform pustules; and/or reversal of stratum granulosum in keritinization dorders when applied to human skin.

\* \* \* \* \*